(12) United States Patent
Koo et al.

(10) Patent No.: US 10,800,735 B2
(45) Date of Patent: Oct. 13, 2020

(54) INTERMEDIATE COMPOUND FOR MANUFACTURING BIXIN ETHYL ESTER AND METHOD OF MANUFACTURING THE SAME

(71) Applicant: MYONGJI UNIVERSITY INDUSTRY AND ACADEMIA COOPERATION FOUNDATION, Yongin-si, Gyeonggi-do (KR)

(72) Inventors: Sangho Koo, Yongin-si (KR); Dahye Kim, Seoul (KR); Mohammad Shariful Alam, Yongin-si (KR)

(73) Assignee: MYONGJI UNIVERSITY INDUSTRY AND ACADEMIA COOPERATION FOUNDATION, Yongin-si (KR)

( * ) Notice: Subject to any disclaimer, the term of this patent is extended or adjusted under 35 U.S.C. 154(b) by 0 days.

(21) Appl. No.: 16/510,243

(22) Filed: Jul. 12, 2019

(65) Prior Publication Data

US 2020/0262786 A1    Aug. 20, 2020

(30) Foreign Application Priority Data

Feb. 20, 2019 (KR) .......................... 10-2019-0020099

(51) Int. Cl.
| | | |
|---|---|---|
| C07C 317/24 | (2006.01) | |
| C07C 67/30 | (2006.01) | |
| C07C 69/34 | (2006.01) | |
| C07C 315/02 | (2006.01) | |
| C07C 317/44 | (2006.01) | |
| C07C 67/465 | (2006.01) | |
| C07C 67/313 | (2006.01) | |
| C07D 277/76 | (2006.01) | |

(52) U.S. Cl.
CPC ............ *C07C 317/24* (2013.01); *C07C 67/30* (2013.01); *C07C 67/313* (2013.01); *C07C 67/465* (2013.01); *C07C 69/34* (2013.01); *C07C 315/02* (2013.01); *C07C 317/44* (2013.01); *C07D 277/76* (2013.01)

(58) Field of Classification Search
None
See application file for complete search history.

(56) References Cited

U.S. PATENT DOCUMENTS

2006/0194973 A1*  8/2006 Gainer ................. A61K 9/19
                                                       554/121

FOREIGN PATENT DOCUMENTS

| KR | 10-0733023 B1 | 6/2007 |
| KR | 10-1315904 B1 | 10/2013 |
| KR | 10-1566159 B1 | 11/2015 |

OTHER PUBLICATIONS

Pattenden ("Carotenoids and Related Compounds. Part XXVI. Synthesis of Methyl Natural Bixin" J. Chem. Soc. (C), 1970, p. 235-241) (Year: 1970).*

(Continued)

*Primary Examiner* — Amy C Bonaparte
(74) *Attorney, Agent, or Firm* — Sughrue Mion, PLLC

(57) ABSTRACT

The present invention relates to a method of manufacturing norbixin or bixin ethyl ester, which is a carotenoid-based compound, from a novel intermediate compound. When the novel intermediate compound is used, it is possible to manufacture norbixin or bixin ethyl ester in high yield through a simple process.

7 Claims, 5 Drawing Sheets

(56) References Cited

OTHER PUBLICATIONS

Von O. Isler, et al., "139. Synthesen in der Carotinoid-Reihe. Anwendung der Wittig-Reaktion zur Synthese von Estern des Bixins and Crocetins", Helvetica Chimica Acta., 1957, pp. 1242-1249, No. 139.
Eunho Choi, et al., "Expeditions and Practical Synthesis of Lycopene", Communications, Adv. Symth. Catal., 2008, pp. 365-369, vol. 350.
Jeongae Choi, et al., "A chain extension method for apocarotenoids; lycopene and lycophyll syntheses", Archives of Biochemistry and Biophysics, 2015, pp. 142-150, vol. 572.
Dahye Kim, et al., "Bromoacetate Olefination Protocol for Norbixin and Julia-Kocienski Olefination for Its Ester Syntheses", ACS Publication, 2019, pp. 10019-10024, vol. 4.
Marie E. Krafft; "The Darzens condensation of a,β-unsaturated aldehydes and ketones"; ScienceDirect; Tetrahedron Letters, vol. 52, Issue 12, Mar. 23, 2011, pp. 1277-1280.
Galina V. Kryshtal et al; Efficient syntheses of C20-carotene and crocetin (descrocetin) esters promoted by an acidic ionic liquid; ScienceDirect; Tetrahedron Letters, vol. 53, Issue 37, Sep. 12, 2012, pp. 4971-4973.
Office Communication (Decision to Grant) dated Apr. 8, 2020 for related Korean Patent Application No. 10-2019-0020099.

* cited by examiner

INTERMEDIATE COMPOUND FOR MANUFACTURING BIXIN ETHYL ESTER AND METHOD OF MANUFACTURING THE SAME

This work was supported by the National Research Foundation of Korea through the Basic Science Research Program (NRF-2016R1A2B4007684).

BACKGROUND OF THE INVENTION

1. Field of the Invention

The present invention relates to a novel intermediate compound for manufacturing norbixin or bixin ethyl ester and a method of manufacturing the same. More specifically, the present invention relates to a novel intermediate compound and a method of manufacturing the same, in which norbixin or bixin ethyl ester, which is a carotenoid-based compound, is manufactured in high yield from a novel intermediate compound through a simple process.

2. Description of the Related Art

Colorants may be classified into natural colorants or synthetic colorants, and are used in various fields such as those of food, cosmetics, and textile dyeing. Synthetic colorants have come to be used extensively in place of natural colorants because of their high coloring rate, stability, and low cost. However, the use of synthetic colorants is limited due to safety issues regarding toxicity to humans. Due to the safety issues with synthetic colorants, interest in natural colorants used for food colorants has been increasing recently.

Unlike synthetic colorants, natural colorants are safe, have a variety of color tones, and are used as coloring agents in all foods because the natural colorants mostly include food ingredients that are edible. However, the natural colorants have drawbacks in that the range of raw materials thereof is limited, in that costs are high and the raw materials are not easy to obtain depending on the kind of raw material.

Norbixin is a polar carotenoid-based compound extracted from the seed of the tropical plant *Bixa orellana* L., which is also known as Annatto, and is widely used as a coloring agent for food and cosmetics. Norbixin has the structural feature of conjugated polyene acid, which endows the natural dye with antioxidant and antimicrobial activities. Unlike the general belief that this red pigment will have good water-solubility, it is scarcely soluble in water, which allows isolation of the polar carotenoid by extraction from an aqueous acidic solution. Also, bixin ethyl ester is a coloring agent derived from the seed of the tropical plant *Bixa orellana* L., which is known as Annatto, and is a carotenoid-based compound having a yellow or orange color. When saponification is performed with an alkaline solution, the water-soluble form of bixin ethyl ester is norbixin.

With respect to the organic synthesis of bixin ethyl ester, a method using the Wittig olefination of $C_{20}$ crocetin dialdehyde 4, represented by Chemical Formula 4, and phosphorus ylene derived from ethyl bromoacetate 5, represented by Chemical Formula 5, was reported more than a half century ago (Helvetica Chimica Acta 1957, 40, 1242-1249). The above-described synthesis method is not practical because $C_{20}$ dialdehyde 4, which is represented by Chemical Formula 4 and is difficult to synthesize, must be synthesized and used.

Therefore, the present inventors have made extensive efforts to overcome the problems with the prior art, and as a result, have invented a novel intermediate for easily manufacturing norbixin or bixin ethyl ester used as a natural colorant, and found that when norbixin or bixin ethyl ester is manufactured using the novel intermediate, norbixin or bixin ethyl ester is obtained in high yield through a simple process, whereby the present invention was completed.

DOCUMENTS OF RELATED ART (Patent Document 1) KR10-0733023 B

SUMMARY OF THE INVENTION

Accordingly, the present invention has been made keeping in mind the above problems occurring in the related art, and a main object of the present invention relates to a novel intermediate compound for manufacturing norbixin or bixin ethyl ester in high yield through a simple process, and a method of manufacturing the same.

Another object of the present invention is to provide a method of manufacturing norbixin or bixin ethyl ester using the novel intermediate compound.

According to an aspect of the present invention, the present invention provides a bromohydrin compound 7 represented by the following Chemical Formula 7.

[Chemical Formula 7]

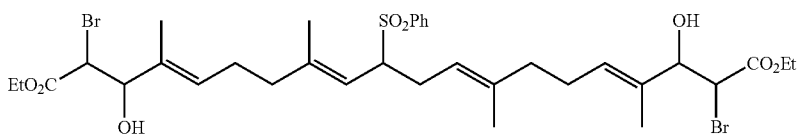

The present inventors found that, in order to manufacture the bromohydrin compound 7 represented by Chemical Formula 7, $C_{20}$ dialdehyde 6, represented by Chemical Formula 6, which may be manufactured using double allylic oxidation of the coupling product between geranyl sulfone and geranyl bromide (Advanced Synthesis & Catalysis 2008, 350, 365-369), is a substitute capable of replacing $C_{20}$ crocetin dialdehyde 4, represented by Chemical Formula 4, in a sulfone olefination protocol. In order to find a suitable anion-stabilizer that induces a coupling reaction with aldehyde and acts as a leaving group, the present inventors manufactured the bromohydrin compound 7 represented by Chemical Formula 7 through olefination using ethyl bromoacetate 5 represented by Chemical Formula 5 and $C_{20}$ dialdehyde 6 represented by Chemical Formula 6.

[Chemical Formula 4]

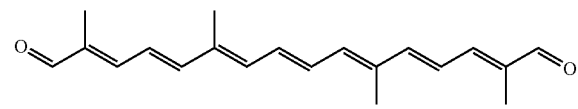

4

[Chemical Formula 5]

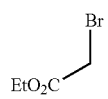

5

[Chemical Formula 6]

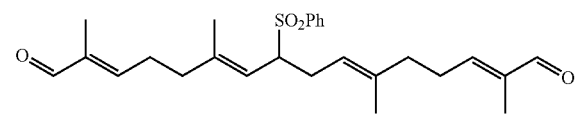

6

The method of manufacturing the bromohydrin compound 7 represented by Chemical Formula 7 using ethyl bromoacetate 5 represented by Chemical Formula 5 and $C_{20}$ dialdehyde 6 represented by Chemical Formula 6 is as follows.

According to another aspect of the present invention, the present invention provides a method of manufacturing a bromohydrin compound 7 of the following Chemical Formula 7, which includes the following steps:

(a) mixing a metal-amide base with a compound represented by the following Chemical Formula 5 to manufacture a first mixture; and (b) adding dialdehyde represented by the following Chemical Formula 6 to the first mixture and performing a reaction, thus obtaining the bromohydrin compound represented by the following Chemical Formula 7.

[Chemical Formula 5]

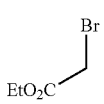

5

[Chemical Formula 6]

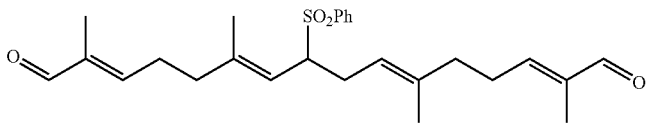

6

[Chemical Formula 7]

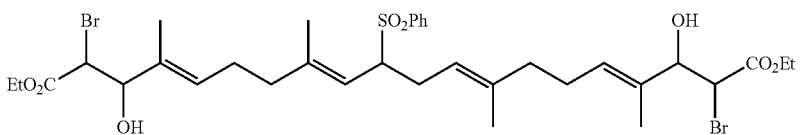

7

The specific method of manufacturing the bromohydrin compound of Chemical Formula 7 is as follows. First, the metal-amide base is mixed with the compound represented by Chemical Formula 5 to thus manufacture the first mixture. Dialdehyde 6 represented by Chemical Formula 6 is added to the first mixture and stirring is performed at −70 to 80° C. for 3 to 5 hours, thus manufacturing a second mixture. The stirred second mixture is quenched with hydrochloric acid (HCl) and extracted with ethyl acetate (EtOAc). Then, the extract may be washed, dried, filtered, and concentrated to obtain the bromohydrin compound represented by Chemical Formula 7.

In the method of manufacturing the bromohydrin compound 7 of the present invention, the metal-amide base in the step (a) is LDA (lithium diisopropylamide) or LiHMDS (lithium bis(trimethylsilyl)amide).

According to an embodiment of the present invention, it was confirmed that the bromohydrin compound 7 represented by Chemical Formula 7 is manufactured in the reaction using LDA or LiHMDS as a metal-amide base, but that the bromohydrin compound 7 represented by Chemical Formula 7 is not manufactured in the reaction using KHMDS as the metal-amide base. These results imply that the metal-amide base is an important constitutional element in the manufacture of the bromohydrin compound 7 represented by Chemical Formula 7, which is a novel intermediate compound according to the present invention (see Experimental Example 1 and Table 1).

In the method of manufacturing the bromohydrin compound 7 represented by Chemical Formula 7, the bromohydrin compound is manufactured in high yield, but epoxide products (Chemical Formulas 8 and 9) that do not generate norbixin are also generated.

[Chemical Formula 8]

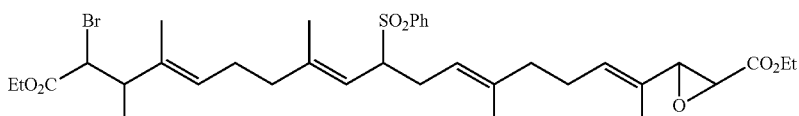

8

[Chemical Formula 9]

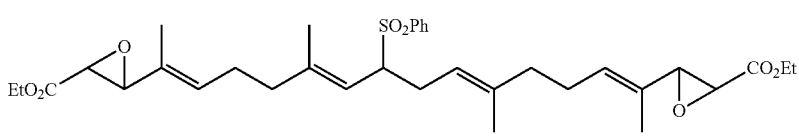

9

Accordingly, in order to increase the efficiency of the process, a method of manufacturing a bromohydrin compound while reducing the amount of epoxide products has been devised. The specific method thereof is as follows.

According to another aspect of the present invention, there is provided a method of manufacturing the bromohydrin compound of the following Chemical Formula 7, which includes the following steps:

(a) mixing a metal-amide base with a compound represented by the following Chemical Formula 5 to manufacture a first mixture, (b) mixing the first mixture with a magnesium salt to manufacture a second mixture, and (c) adding dialdehyde represented by the following Chemical Formula 6 to the second mixture and performing a reaction to thus obtain the bromohydrin compound represented by the following Chemical Formula 7.

[Chemical Formula 5]

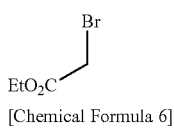

5

[Chemical Formula 6]

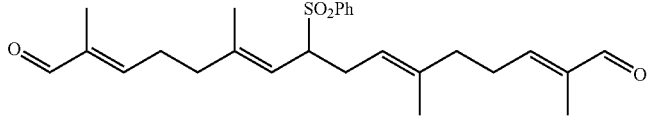

6

[Chemical Formula 7]

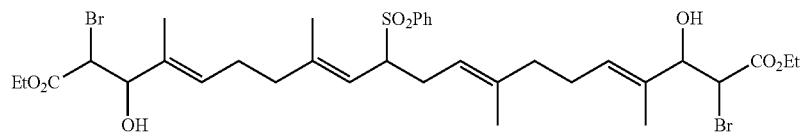

The specific method of manufacturing the bromohydrin compound of Chemical Formula 7 is as follows. First, the metal-amide base is mixed with the compound represented by the Chemical Formula 5 to manufacture the first mixture. A magnesium salt is added to the first mixture and stirring is performed, thus manufacturing the second mixture. Dialdehyde 6, represented by Chemical Formula 6, is added to the second mixture to manufacture a third mixture, and stirring is performed. The stirred third mixture is quenched with hydrochloric acid (HCl) and extracted with ethyl acetate. Then, the extract may be dried, filtered, and concentrated to obtain the bromohydrin compound represented by Chemical Formula 7.

In the method of manufacturing the bromohydrin compound 7 of Chemical Formula 7 of the present invention, the magnesium salt of the step (b) is $MgBr_2$ (magnesium bromide) or $Mg(N-i-Pr_2)_2$.

According to an embodiment of the present invention, it was confirmed that none of the bromohydrin compound 7 represented by Chemical Formula 7 and the mono- and di-epoxide products 8 and 9 represented by Chemical Formulas 8 and 9 were generated in the reaction using LDA as the metal-amide base and $BF_3.OEt_2$ as an additive, but that the epoxide product was not generated and only the bromohydrin compound represented by Chemical Formula 7 was generated in the reaction using $Mg(N-i-Pr_2)_2$ or $MgBr_2$, which are magnesium salts, as an additive. These results imply that a magnesium enolate is an important constitutional element in the manufacture of only the bromohydrin compound while reducing the generation of epoxide products (see Experimental Example 1 and Table 1).

According to another aspect of the present invention, the present invention provides a method of manufacturing norbixin represented by the following Chemical Formula 1, which includes the following steps:

(a) adding pyridinium p-toluene sulfonate and ethyl vinyl ether to the bromohydrin compound represented by the following Chemical Formula 7 to thus obtain 1-ethoxyethyl ether represented by the following Chemical Formula 10, and (b) adding cyclohexane and benzene to the 1-ethoxyethyl ether obtained in the step (a) and performing a reaction with a base, thus obtaining norbixin represented by Chemical Formula 1.

[Chemical Formula 7]

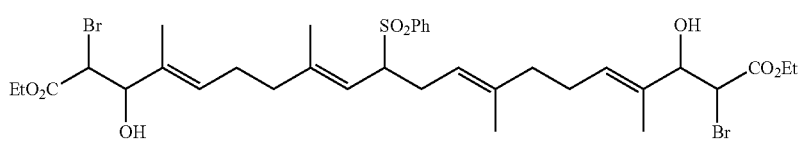

[Chemical Formula 10]

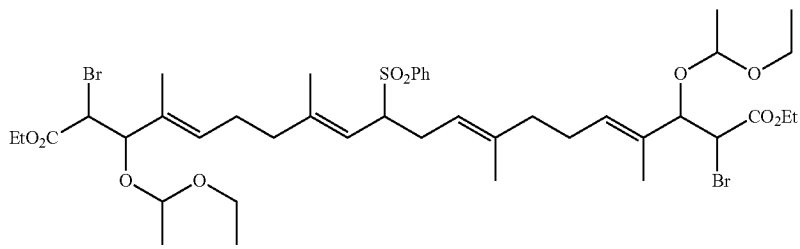

[Chemical Formula 1]

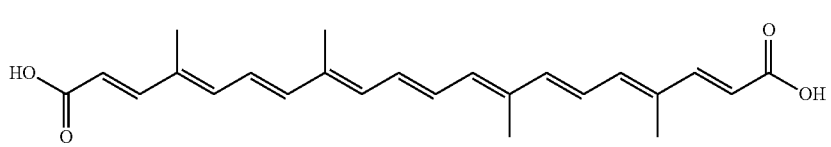

As the base used in the step (b), any base selected from the group consisting of MeOK, EtOK, t-BuOK, MeONa, EtONa, KOMe, and t-BuONa may be used. In the embodiment of the present invention, KOMe is used, without being limited thereto.

In olefination using the manufacturing method, after 1-ethoxyethyl ether 10 represented by Chemical Formula 10 is generated to directly produce norbixin 1 using bromohydrin 7 represented by Chemical Formula 7 (see FIG. 3), norbixin 1 is obtained in high yield.

According to another aspect of the present invention, the present invention provides an ester compound represented by the following Chemical Formula 15.

[Chemical Formula 15]

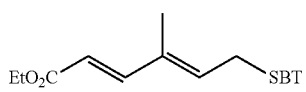
15

According to another aspect of the present invention, there is provided a method of manufacturing an ester compound represented by the following Chemical Formula 15, which includes the following steps:

(a) adding sodium hydride (NaH) to a solution in which tetrahydrofuran and (2-ethoxy-2-oxoethyl)triphenylphosphonium bromide are stirred to thus manufacture a mixture; and (b) adding aldehyde represented by the following Chemical Formula 13 to the mixture and performing a reaction to obtain the ester compound represented by Chemical Formula 15.

[Chemical Formula 13]

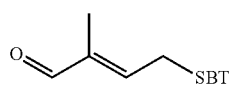
13

[Chemical Formula 15]

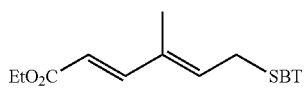
15

The specific method of manufacturing the ester compound of Chemical Formula 15 is as follows. First, sodium hydride is added to a solution in which tetrahydrofuran (THF) and (2-ethoxy-2-oxoethyl)triphenylphosphonium bromide are stirred to thus manufacture the mixture. Aldehyde 13, represented by Chemical Formula 13 (Archives of Biochemistry and Biophysics 2015, 572, 142-150), is added to the mixture, stirred, diluted with ethyl acetate, and quenched with a 10% aqueous ammonium chloride solution, thus obtaining a crude product from an organic layer. The obtained crude product may be purified to obtain the ester compound 15 represented by Chemical Formula 15.

According to another aspect of the present invention, the present invention provides a sulfone compound represented by the following Chemical Formula 11.

[Chemical Formula 11]

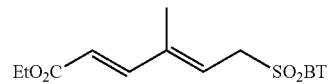
11

According to another aspect of the present invention, the present invention provides a method of manufacturing a sulfone compound 11 represented by the following Chemical Formula 11. The manufacturing method includes mixing and reacting an ester compound represented by the following Chemical Formula 15 and a solution containing acetonitrile.

[Chemical Formula 11]

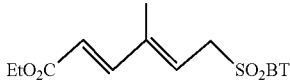
11

[Chemical Formula 15]

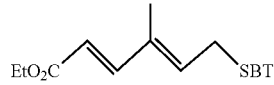
15

The solution containing acetonitrile may be manufactured by mixing a mixture of urea-$H_2O_2$ and phthalic anhydride with acetonitrile.

Further, the ester compound represented by Chemical Formula 15 may be manufactured by adding a compound represented by the following Chemical Formula 13 to a mixture containing tetrahydrofuran, (2-ethoxy-2-oxoethyl)triphenylphosphonium bromide, and sodium hydride and performing a reaction.

[Chemical Formula 13]

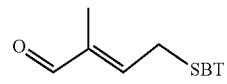
13

That is, the sulfone compound 11 represented by Chemical Formula 11 may be manufactured using a process which includes (a) manufacturing a solution in which urea-$H_2O_2$, phthalic anhydride, and acetonitrile are mixed with each other, and (b) adding a solution of the ester compound represented by Chemical Formula 15 to the solution of the step (a) and performing a reaction to thus obtain the sulfone compound represented by Chemical Formula 11.

The specific method of manufacturing the sulfone compound of Chemical Formula 11 is as follows. First, the solution of the ester compound 15 represented by the following Chemical Formula 15 is mixed with the solution in which urea-$H_2O_2$, phthalic anhydride, and acetonitrile are mixed with each other, thus manufacturing a mixture. After the mixture is stirred, the solvent is removed to obtain a crude product. The obtained crude product may be purified to obtain the sulfone compound 11 represented by Chemical Formula 11.

According to another aspect of the present invention, the present invention provides a compound represented by the following Chemical Formula 16.

[Chemical Formula 16]

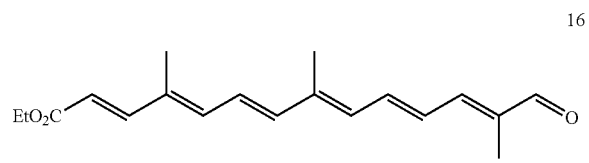

16

According to another aspect of the present invention, the present invention provides a method of manufacturing a compound 16 represented by the following Chemical Formula 16.

(a) stirring a sulfone compound represented by Chemical Formula 11 and an aldehyde compound represented by the following Chemical Formula 12 to thus manufacture a mixture, and (b) adding DBU (1,8-diazabicycloundec-7-ene) to the mixture stirred in the step (a) and performing a reaction, thus obtaining the compound represented by the following Chemical Formula 16.

[Chemical Formula 11]

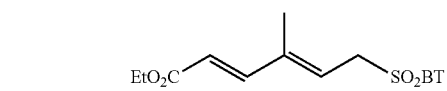

11

[Chemical Formula 12]

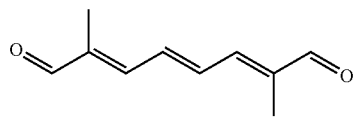

12

[Chemical Formula 16]
-continued

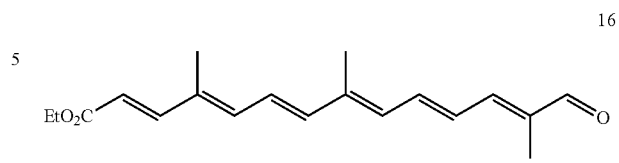

16

The specific method of manufacturing the compound represented by Chemical Formula 16 is as follows. First, DBU (1,8-diazabicycloundec-7-ene) is added to the solution in which the sulfone compound 11 represented by Chemical Formula 11 and the aldehyde compound 12 represented by the following Chemical Formula 12 are stirred, thus manufacturing the mixture. The mixture is stirred, quenched with a 10% aqueous ammonium chloride solution, and extracted with dichloromethane, thus obtaining a crude product. The obtained crude product may be purified to obtain the compound 16, represented by Chemical Formula 16.

According to another aspect of the present invention, there is provided a method of manufacturing bixin ethyl ester represented by the following Chemical Formula 2. The manufacturing method includes mixing a sulfone compound represented by the following Chemical Formula 11 with a compound represented by the following Chemical Formula 12 or a compound represented by the following Chemical Formula 16. Further, the above-mentioned manufacturing method may further include adding DBU (1,8-diazabicycloundec-7-ene) to a mixture in which the sulfone compound represented by Chemical Formula 11 is mixed with the compound represented by Chemical Formula 12 or the compound represented by Chemical Formula 16, and performing a reaction.

[Chemical Formula 11]

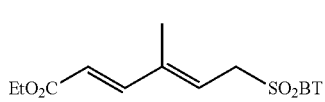

11

[Chemical Formula 12]

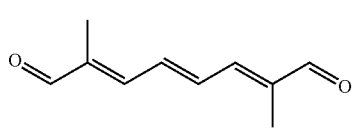

12

[Chemical Formula 16]

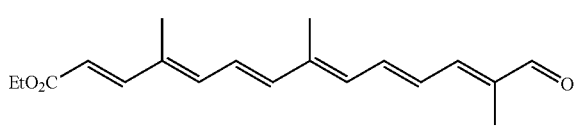

16

[Chemical Formula 2]

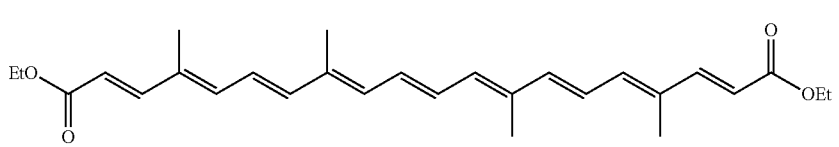

2

That is, the method of manufacturing bixin ethyl ester 2 represented by Chemical Formula 2 may include (a) stirring the sulfone compound represented by Chemical Formula 11 and the compound represented by Chemical Formula 16 to manufacture a mixture, and (b) adding DBU (1,8-diazabicycloundec-7-ene) to the mixture stirred in the step (a) and performing a reaction to thus obtain bixin ethyl ester represented by Chemical Formula 2.

The specific method of manufacturing bixin ethyl ester represented by Chemical Formula 2 is as follows. First, DBU (1,8-diazabicycloundec-7-ene) is added to a solution in which the sulfone compound 11 represented by Chemical Formula 11 and the compound 16 represented by Chemical Formula 16 are stirred and mixing and reaction are performed. The mixture is reacted for 20 to 26 hours and then quenched with a 10% aqueous ammonium chloride solution ($NH_4Cl$). The quenched mixture may be extracted, dried, filtered, and concentrated to obtain a crude product. The crude product may then be purified to obtain bixin ethyl ester 2 represented by Chemical Formula 2.

The compound represented by Chemical Formula 16 may be manufactured by adding DBU (1,8-diazabicycloundec-7-ene) to the sulfone compound represented by Chemical Formula 11 and the aldehyde compound represented by Chemical Formula 12 and performing a reaction.

Further, the method of manufacturing bixin ethyl ester 2 represented by Chemical Formula 2 may include (a) stirring the sulfone compound represented by Chemical Formula 11 and the compound represented by Chemical Formula 12 to manufacture a mixture, and (b) adding DBU (1,8-diazabicycloundec-7-ene) to the mixture stirred in the step (a) and performing a reaction, thus obtaining bixin ethyl ester represented by Chemical Formula 2.

The specific method of manufacturing bixin ethyl ester represented by Chemical Formula 2 is as follows. First, DBU (1,8-diazabicycloundec-7-ene) is added to the solution in which the sulfone compound 11 represented by Chemical Formula and the aldehyde compound 12 represented by Chemical Formula 12 are stirred, and mixing and reaction are performed. The mixture is reacted for 10 to 14 hours and then quenched with a 10% aqueous ammonium chloride solution ($NH_4Cl$). The quenched mixture may be extracted, dried, filtered, and concentrated to obtain a crude product. The crude product may be purified to obtain bixin ethyl ester 2 represented by Chemical Formula 2.

The synthesis of bixin ethyl ether 2 represented by Chemical Formula 2 according to the present invention is performed through Julia-Kocienski olefination of BT-sulfone (benzothiazolyl-sulfone) 11, which is a novel intermediate and is represented by Chemical Formula 11, and $C_{10}$ dialdehyde 12 represented by Chemical Formula 12 (see FIG. 4). BT-sulfone 11 represented by Chemical Formula 11 is generated through an oxidation reaction using phthalic anhydride and urea-$H_2O_2$ after chain-extended $C_7$ dienyl BT-sulfide 15 (yield of 91%) represented by Chemical Formula 15 is generated using a Wittig reaction of $C_5$ BT-sulfide (benzothiazolyl-sulfide) 13, which is conventionally known, and ethyl 2-(triphenyl-$\lambda^5$-phosphaneylidene)acetate.

Julia-Kocienski olefination of 2 equivalents of BT-sulfone 11 represented by Chemical Formula 11 and 1 equivalent of $C_{10}$ dialdehyde 12 represented by Chemical Formula 12 is performed using DBU in $CH_2Cl_2$ at 25° C., thus generating a mono-olefination compound 16 (yield of 70%) represented by Chemical Formula 16. When 4 equivalents of BT-sulfone 11 represented by Chemical Formula 11 are used with respect to dialdehyde 12 represented by Chemical Formula 12, the mono-olefination compound 16 (yield of 53%) represented by Chemical Formula 16 and bixin ethyl ester 2 (yield of 12%) represented by Chemical Formula 2 are obtained.

Further, when the Julia-Kocienski olefination is performed using the produced mono-olefination compound 16 represented by Chemical Formula 16 and BT-sulfone 11 (2 equivalent) represented by Chemical Formula 11, bixin ethyl ester 2 represented by Chemical Formula 2 is obtained in a yield of 70% (see FIG. 5).

The bromohydrin compound of Chemical Formula 7, which is newly manufactured according to the present invention, may be used to manufacture norbixin, which is a carotenoid-based compound, in high yield using only a two-step process.

Further, the sulfone compound of Chemical Formula 11, which is newly manufactured according to the present invention, may be reacted with the aldehyde compound of Chemical Formula 12, thus manufacturing a compound, which is a novel intermediate compound and is represented by Chemical Formula 16, and bixin ethyl ester.

Further, the compound represented by Chemical Formula 16 may be reacted with the sulfone compound represented by Chemical Formula 11, thus manufacturing bixin ethyl ester, which is a carotenoid-based compound, in high yield.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
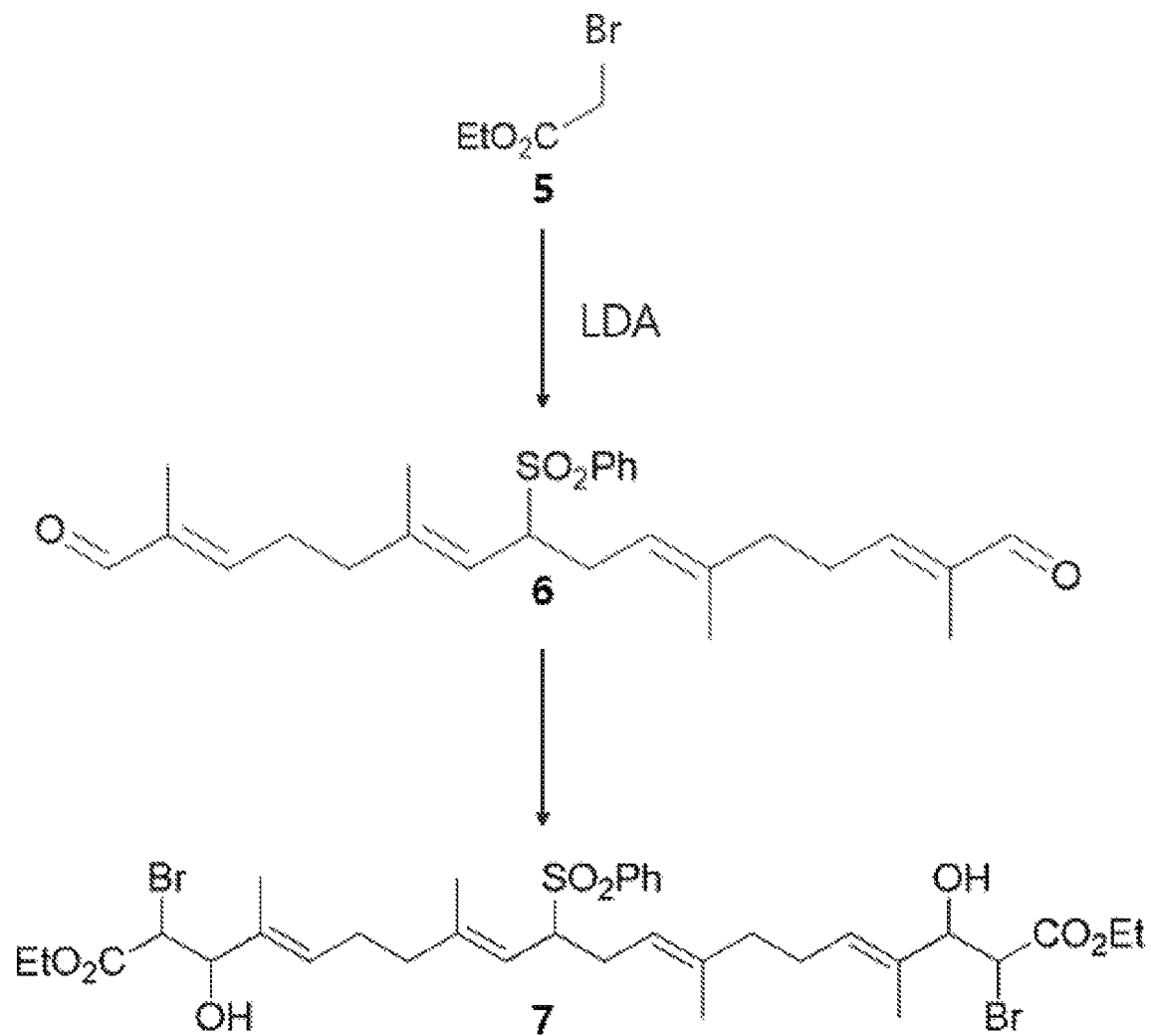
FIG. 1 shows the synthesis scheme of a novel intermediate compound represented by Chemical Formula 7 according to an embodiment of the present invention.
Figure 2:
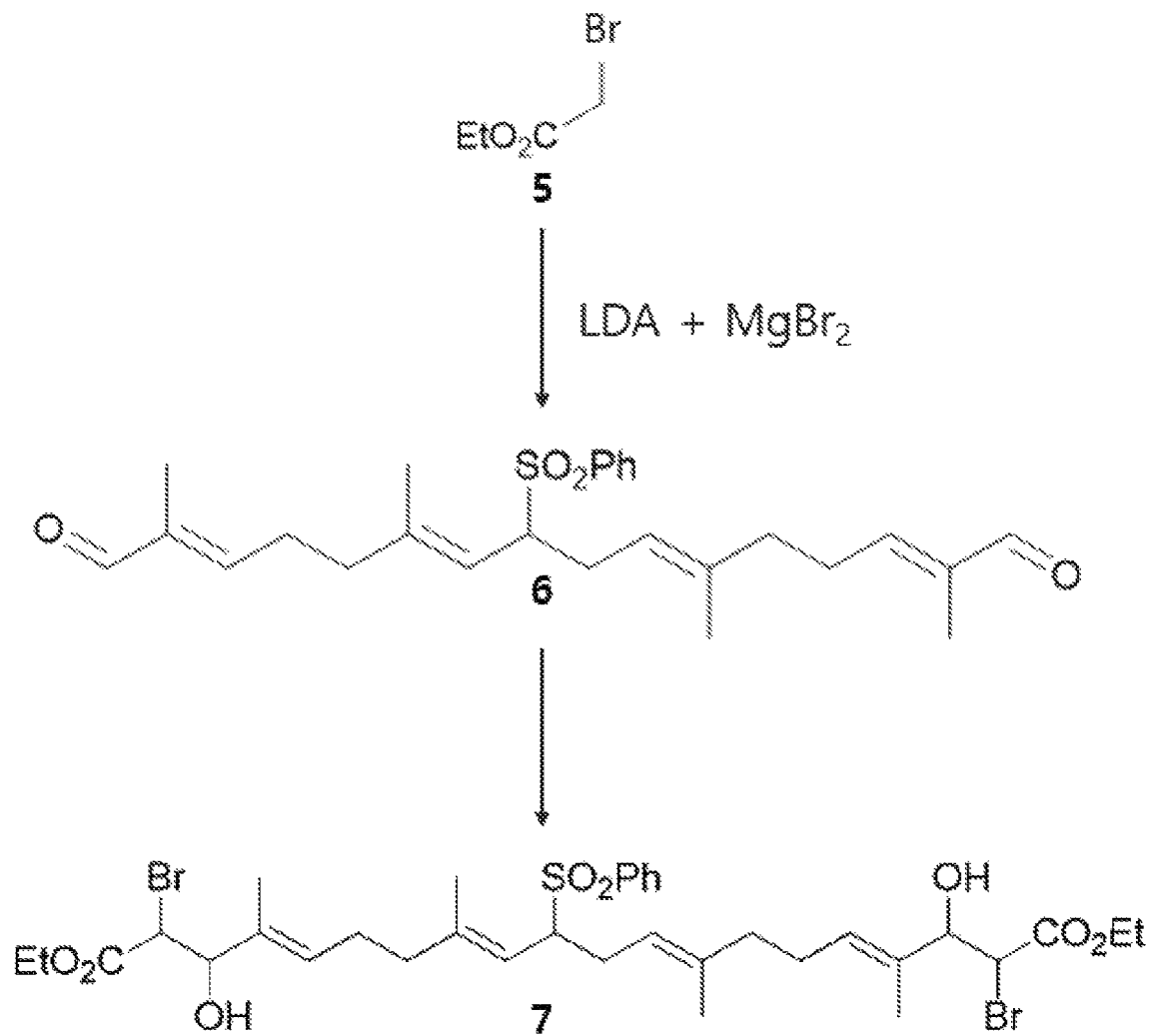
FIG. 2 shows the synthesis scheme of the novel intermediate compound represented by Chemical Formula 7 according to an embodiment of the present invention.
Figure 3:
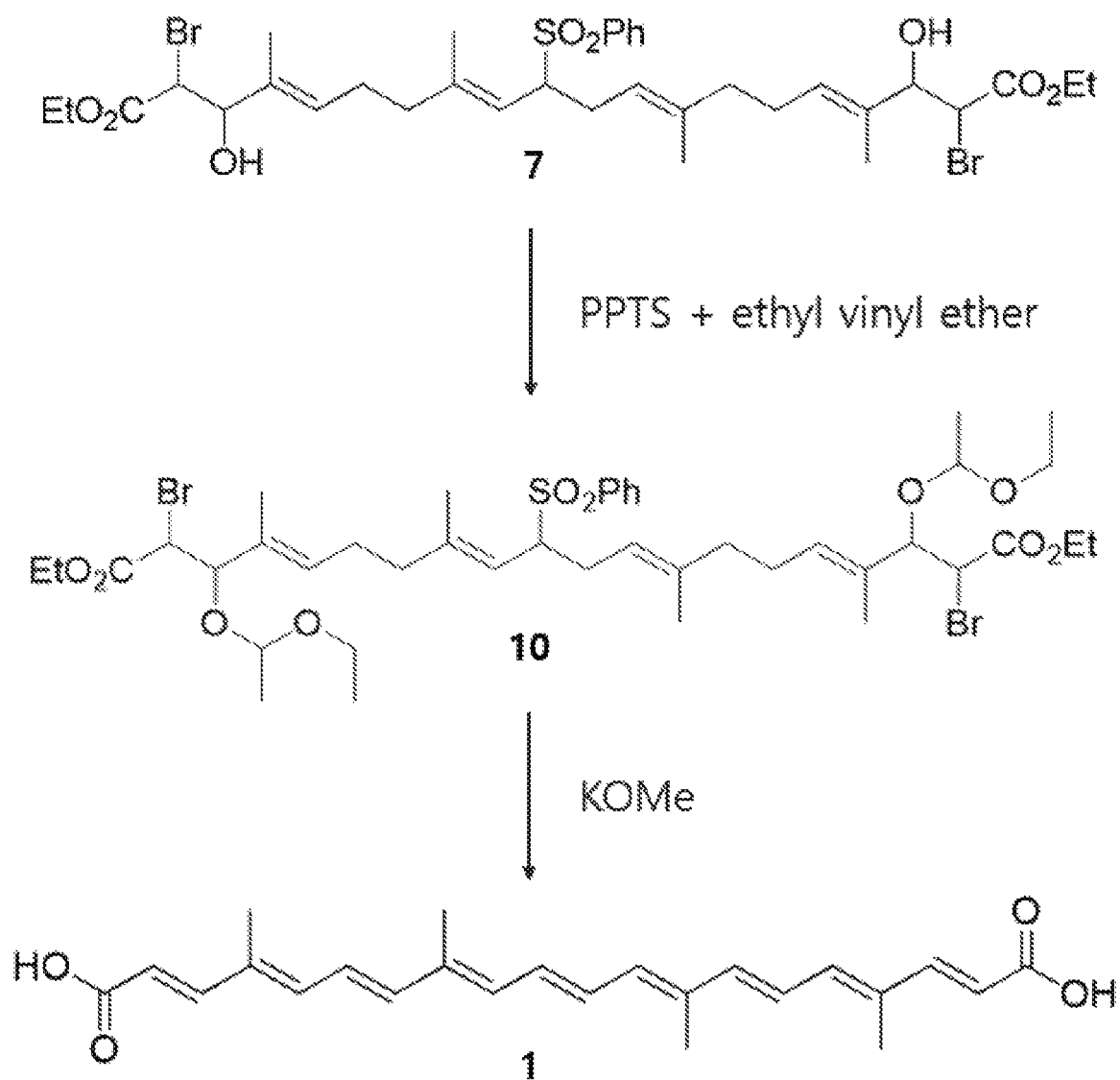
FIG. 3 shows the synthesis scheme of norbixin using the novel intermediate compound represented by Chemical Formula 7 of the present invention.
Figure 4:
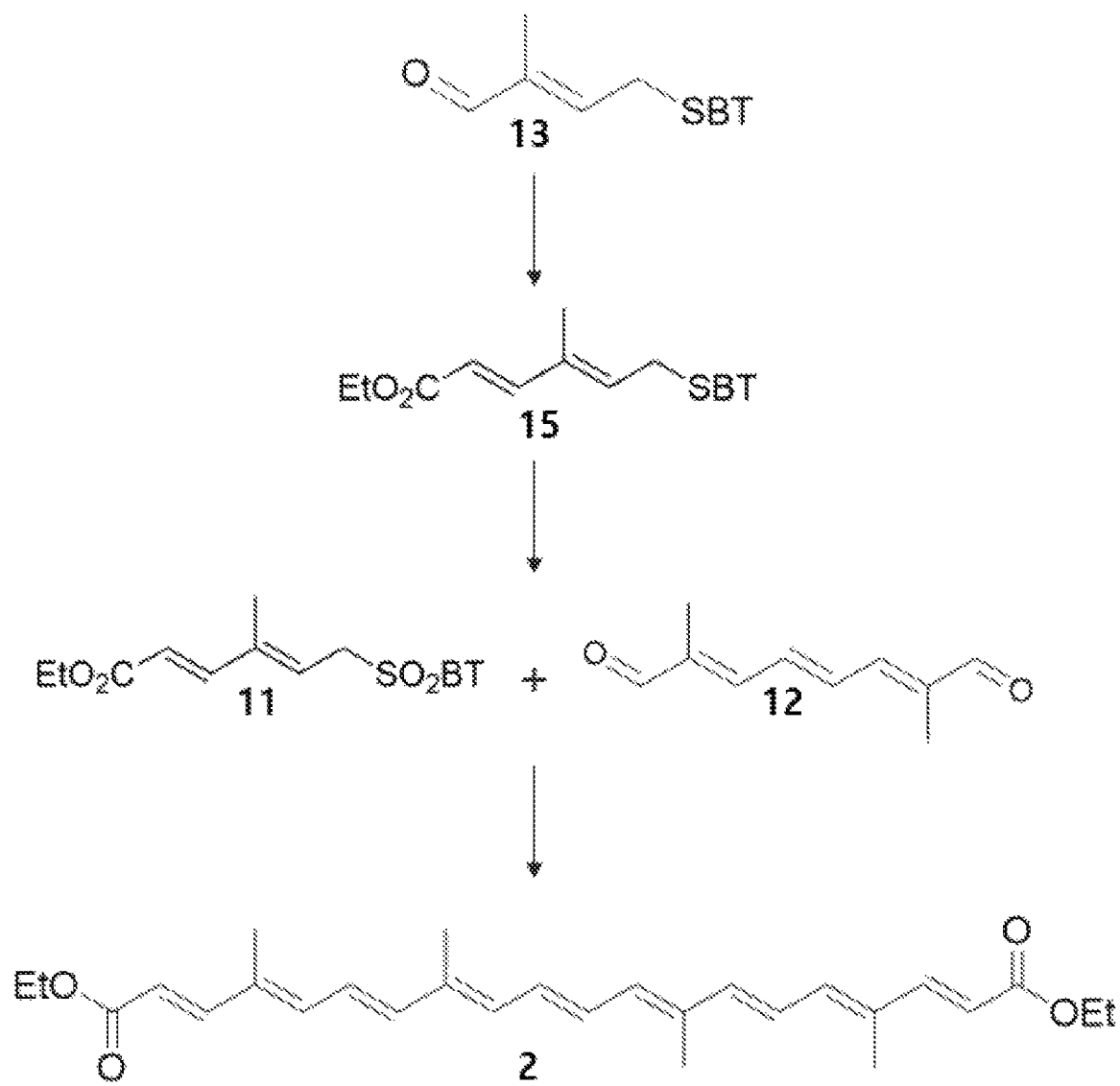
FIG. 4 shows the synthesis scheme of bixin ethyl ester according to an embodiment of the present invention.
Figure 5:
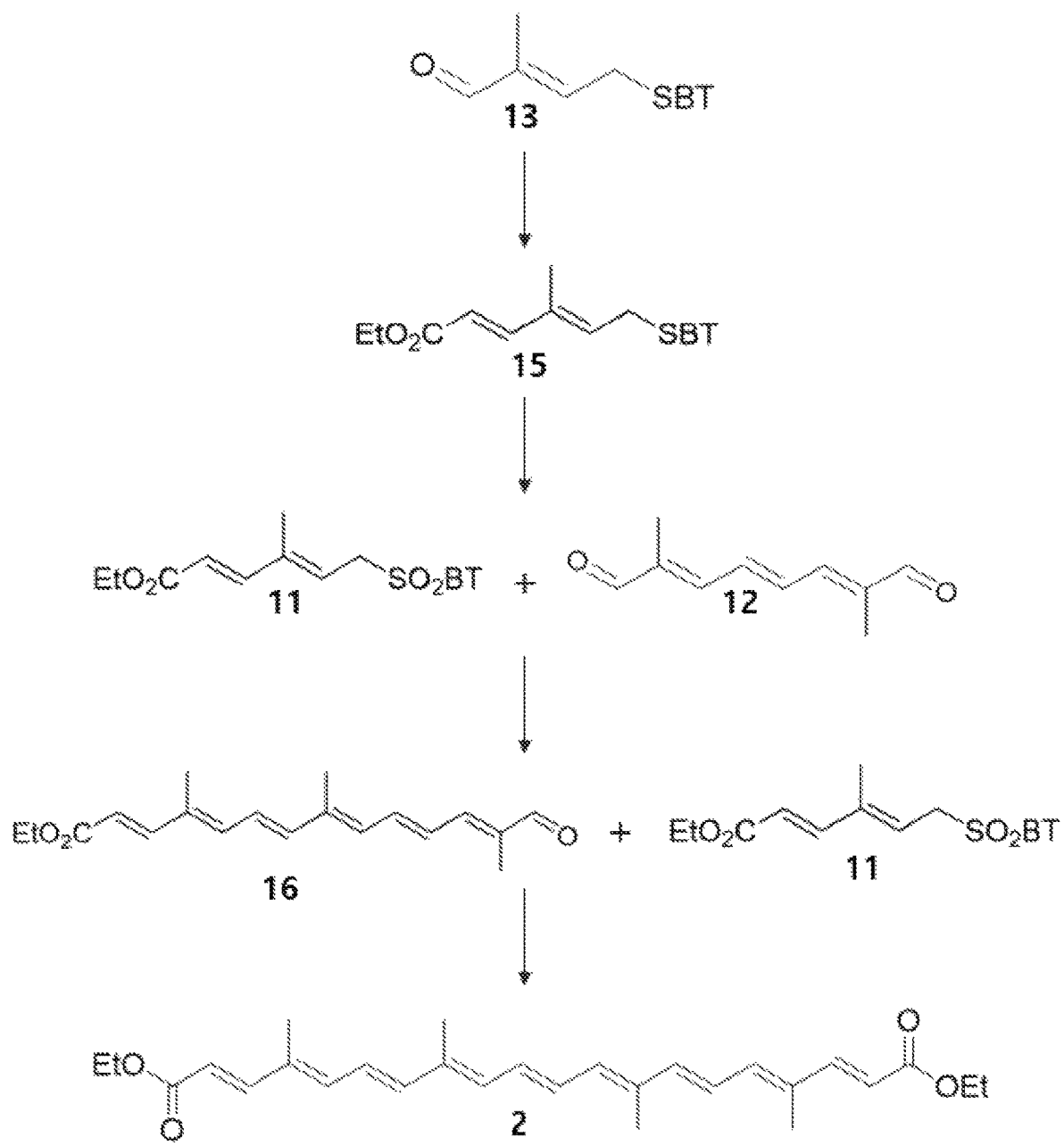
FIG. 5 shows the synthesis scheme of bixin ethyl ester according to an embodiment of the present invention.

Hereinafter, the present invention will be described in more detail with reference to Examples. These Examples are only for illustrating the present invention, and thus the scope of the present invention is not to be construed as being limited by these Examples.

$^1$H- and $^{13}$C-NMR spectra were respectively recorded on a 400 MHz and 100 MHz NMR spectrometer in $CDCl_3$ with tetramethylsilane as an internal reference unless noted otherwise. High resolution mass spectroscopy was performed using magnetic sector analyzer. The column chromatography was performed by the method of Still with silica gel 60, 70-230 mesh ASTM using a gradient mixture of EtOAc/hexanes. Reactions were performed in a well-dried flask under argon atmosphere unless noted otherwise.

Example 1-1: Preparation of (4E,8E,12E,16E)-Diethyl 2,19-dibromo-3,18-dihydroxy-4,8,13,17-tetramethyl-10-(phenylsulfonyl)icosa-4,8,12,16-tetraenedioate (7), diethyl 3,3'-((2E,6E,10E,14E)-6,11-dimethyl-8-(phenylsulfonyl)hexadeca-2,6,10,14-tetraene-2,15-diyl)bis(oxirane-2-carboxylate) (9)

To a stirred 1.0 M solution of Lithium diisopropylamide in THF/hexanes (7.0 mL, 6.84 mmol, 5.2 equiv.) in THF (20 mL) at −° C. was slowly added ethyl bromoacetate 5 (0.73 mL, 6.57 mmol, 5 equiv.). The mixture was stirred for 20 min, and a solution of dialdehyde 6 (582 mg, 1.32 mmol) in THF (10 mL) was added. The mixture was stirred at −78° C. for 4 hours and quenched with 1M HCl solution. The mixture was warmed to room temperature, extracted with EtOAc, washed with 1M HCl solution, dried over anhydrous $Na_2SO_4$, filtered, and concentrated under reduced pressure. The crude product was purified by silica gel column chromatography to give bromohydrin 7 (470 mg, 0.61 mmol, 46% yield, $R_f$=0.40 in 40% EtOAc/hexane), mono-epoxide 8 (117 mg, 0.17 mmol, 13% yield, $R_f$=0.50), and di-epoxide 9 (60 mg, 0.098 mmol, 7% yield, $R_f$=0.58) as yellow oils.

Example 1-2: Preparation of (4E,8E,12E,16E)-Diethyl 2,19-dibromo-3,18-dihydroxy-4,8,13,17-tetramethyl-10-(phenylsulfonyl)icosa-4,8,12,16-tetraenedioate (7)

To a stirred 1.0 M solution of Lithium diisopropylamide in THF/hexanes (4.8 mL, 4.79 mmol, 5.2 equiv.) in THF (20 mL) at −78° C. was slowly added ethyl bromoacetate 5(0.51 mL, 4.61 mmol, 5 equiv.). The mixture was stirred for 20 min, and magnesium bromide (882 mg, 4.79 mmol, 5.2 equiv.) was added. Stirring was continued for 20 min at −78° C. and a solution of dialdehyde 6(408 mg, 0.92 mmol) in THF (10 mL) was added. The mixture was stirred at −78° C. for 1 hour, warmed to and stirred at room temperature for 5 hours. The mixture was quenched with 1M HCl solution, extracted with EtOAc, dried over anhydrous $Na_2SO_4$, filtered, and concentrated under reduced pressure. The crude product was purified by $SiO_2$ flash column chromatography to give bromohydrin 7(554 mg, 0.71 mmol) in 77% yield as yellow oil.

NMR and IR Analysis Result for compound 7 prepared according to EXAMPLE 1-1 and EXAMPLE 1-2 is as follows. The compound structure is represented by the following Chemical Formula 7.

[Chemical Formula 7]

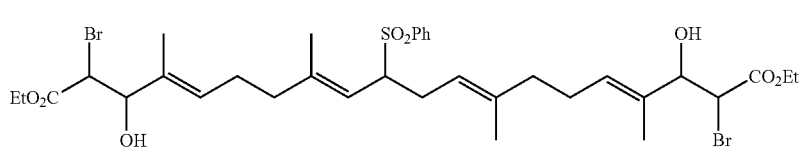

Data for Compound 7: $R_f$=0.40 (2:3 EtOAc/hexane); $^1$H-NMR δ=1.18-1.36 (m, 6H), 1.54-1.66 (m, 12H), 1.94-2.20 (m, 8H), 2.30-2.44 (m, 1H), 2.70-2.86 (m, 1H), 3.70-3.86 (m, 1H), 4.15-4.46 (m, 8H), 4.92-5.10 (m, 2H), 5.43-5.66 (m, 2H), 7.48-7.59 (m, 2H), 7.59-7.68 (m, 1H), 7.78-7.90 (m, 2H) ppm; IR (neat) ν=3474, 2982, 2930, 1737, 1446, 1372, 1297, 1178, 1141, 1081, 1021, 865, 753, 693, 663, 604 $cm^{-1}$; HRMS (FAB) calcd for $C_{34}H_{45}Br_2O_6S$ [$C_{34}H_{49}Br_2O_8S \cdot 2H_2O$] 739.1304, found 739.1310.

NMR and IR Analysis Result for compound 9 prepared according to EXAMPLE 1-1 is as follows. The compound structure is represented by the following Chemical Formula 9.

[Chemical Formula 9]

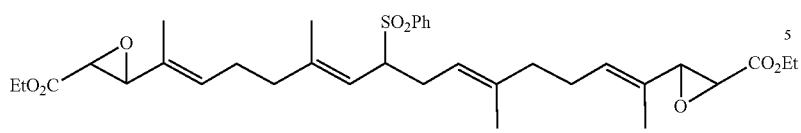

Data for Compound 9: $R_f$=0.58 (2:3 EtOAc/hexane); $^1$H-NMR δ=1.20-1.26 (m, 3H), 1.30 (t, J=7.2 Hz, 6H), 1.45 (s, 3H), 1.47 (s, 3H), 1.56-1.62 (s, 3H), 1.92-2.20 (m, 8H), 2.28-2.44 (m, 1H), 2.82-2.92 (m, 1H), 3.42 (d, J=2.0 Hz, 1H), 3.43 (br s, 1H), 3.50 (d, J=1.6 Hz, 1H), 3.53 (d, J=2.0 Hz, 1H), 3.75 (dt, $J_d$=3.6, $J_t$=10.4 Hz, 1H), 4.16-4.32 (m, 4H), 4.94-5.08 (m, 2H), 5.58-5.67 (m, 2H), 7.50-7.56 (m, 2H), 7.60-7.66 (m, 1H), 7.82-7.87 (m, 2H) ppm; IR (neat) ν=2982, 2937, 1737, 1610, 1446, 1372, 1297, 1252, 1185, 1148, 1081, 1029, 865, 745, 693, 604 cm$^{-1}$; HRMS (FAB) calcd for $C_{28}H_{39}O_5$ [$C_{34}H_{46}O_8S$ $PhSO_2$—$H_2O$] 455.2797, found 455.2803.

Example 2: Preparation of (2E,4E,6E,8E,10E,12E, 14E,16E,18E)-4,8,13,17-Tetramethylicosa-2,4,6,8, 10,12,14,16,18-nonaenedioic acid—Norbixin (1)

To a stirred solution of bromohydrin 7 (437 mg, 0.56 mmol) in $CH_2Cl_2$ (25 mL) at 0° C. were added pyridinium p-toluenesulfonate (28 mg, 0.11 mmol) and ethyl vinyl ether (1.60 mL, 16.80 mmol). The mixture was slowly warmed to and stirred at room temperature for 12 h. The reaction mixture was diluted with $CH_2Cl_2$, washed with aqueous $NaHCO_3$ solution, dried over anhydrous $K_2CO_3$, filtered, and concentrated under reduced pressure to give 1-ethoxyethyl ether 10 (516 mg, 0.56 mmol) as orange yellow oil.

To a stirred solution of 1-ethoxyethyl ether 10 in cyclohexane (20 mL) and benzene (20 mL) was added KOMe (1.18 g, 16.80 mmol, 30 equiv.). The mixture was heated at 80° C. for 18 hours and cooled to room temperature. The mixture was quenched with 1M HCl solution (pH ~1) and extracted thoroughly with $Et_2O$ (60 mL×3) to remove byproducts. The aqueous layer was then extracted with $CH_2Cl_2$ (60 mL×3). Undissolved solid in the aqueous phase was filtered and dissolved in acetone. The organic phases (acetone and $CH_2Cl_2$ solutions) were mixed together, dried over anhydrous $Na_2SO_4$, filtered, and concentrated under reduced pressure to give norbixin 1 (175 mg, 0.46 mmol) in 82% yield in two steps from bromohydrin 7, which was further purified by recrystallization from acetone as dark red solid.

NMR and IR Analysis Result for compound 1 prepared according to EXAMPLE 2 is as follows. The structure of the compound 1 is represented by the following Chemical Formula 1.

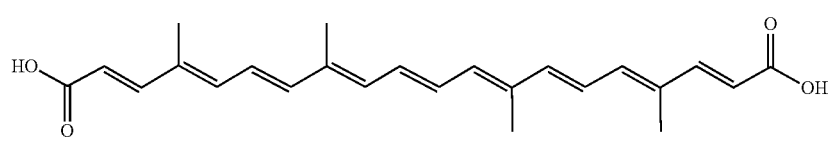

[Chemical Formula 1]

Data for Compound 1: m.p.>300° C.; $^1$H-NMR (DMSO-$d_6$) δ=1.93 (s, 6H), 1.98 (s, 6H), 5.84 (d, J=15.6 Hz, 2H), 6.41-6.51 (m, 2H), 6.60 (d, J=14.8 Hz, 2H), 6.64 (d, J=11.2 Hz, 2H), 6.72 (dd, J=14.8, 11.2 Hz, 2H), 6.76-6.86 (m, 2H), 7.27 (d, J=15.6 Hz, 2H) ppm; $^{13}$C-NMR (DMSO-$d_6$) δ 11.9, 12.0, 116.7, 124.3, 130.9, 132.9, 134.2, 136.3, 138.5, 140.9, 147.6, 167.2 ppm; IR (neat) ν=2915, 1670, 1610, 1558, 1424, 1312, 1282, 1260, 1193, 1141, 1006, 954, 857, 827, 775, 708, 619, 559, 477, 425 cm$^{-1}$; HRMS (FAB) calcd for $C_{24}H_{28}O_4$ 380.1988, found 380.1993.

Example 3: Preparation of (2E,4E)-Ethyl 6-(benzo[d]thiazol-2-ylthio)-4-methylhexa-2,4-dienoate (15)

To a stirred suspension of (2-ethoxy-2-oxoethyl)triphenylphosphonium bromide 14(14.60 g, 34.01 mmol) in THF (100 mL) was added 60% NaH (1.95 g, 48.75 mmol) under argon atmosphere. The mixture was stirred vigorously at room temperature for 1 hour and a solution of aldehyde 13(8.00 g, 32.08 mmol) in THF (20 mL) was added. The mixture was stirred for 24 h, diluted with EtOAc, and quenched by 10% $NH_4Cl$. The organic layer was dried over anhydrous $Na_2SO_4$, filtered, and concentrated under reduced pressure. The crude product was purified by column chromatography ($SiO_2$, eluting with 10-25% EtOAc in hexanes) to give ester 15(9.32 g, 29.18 mmol) in 91% yield as light-yellow viscose liquid.

NMR and IR Analysis Result for compound 15 prepared according to EXAMPLE 3 is as follows. The structure of the compound 15 is represented by the following Chemical Formula 15.

[Chemical Formula 15]

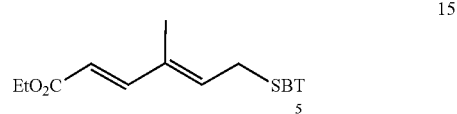

Data for Compound 15: $R_f$=0.68 (1:4 EtOAc/hexane); $^1$H-NMR δ=1.27 (t, J=7.2 Hz, 3H), 1.90 (d, J=0.8 Hz, 3H), 4.14 (d, J=8.4 Hz, 2H), 4.19 (q, J=7.2 Hz, 2H), 5.89 (d, J=15.6 Hz, 1H), 6.09 (dt, $J_d$=0.8 Hz, $J_t$=8.4 Hz, 1H), 7.29 (d, J=15.6 Hz, 1H), 7.25-7.30 (m, 1H), 7.37-7.42 (m, 1H), 7.70-7.74 (m, 1H), 7.84-7.88 (m, 1H) ppm; $^{13}$C-NMR δ=12.2, 14.1, 31.2, 60.1, 118.0, 120.8, 121.4, 124.2, 125.9, 133.2, 135.3, 136.4, 147.7, 152.9, 165.3, 166.7 ppm; IR (neat) ν=3060, 2992, 1706, 1623, 1458, 1394, 1302, 1235, 1170, 990, 848, 755 cm$^{-1}$; HRMS (FAB) calcd for $C_{16}H_{18}NO_2S_2$ 320.0079, found 320.0075.

Example 4: Preparation of (2E,4E)-Ethyl 6-(benzo[d] thiazol-2-ylsulfonyl)-4-methylhexa-2,4-dienoate (11)

The mixture of Urea-$H_2O_2$ (6.80 g, 72.29 mmol) and phthalic anhydride (5.35 g, 36.12 mmol) was stirred in MeCN (70 mL) for 2 hours. A solution of sulfide 15 (3.30 g, 10.33 mmol) in MeCN (15 mL) was added to the above mixture under a cold-water bath. The mixture was stirred at room temperature for 20 h, and most of solvent was removed under reduced pressure. The crude product was dissolved in $CHCl_3$, washed with water, dried over anhydrous $Na_2SO_4$, filtered, and concentrated under reduced pressure. The crude product was purified by $SiO_2$ flash column chromatography (10-50% EtOAc in hexane) to give sulfone 11 (2.95 g, 8.39 mmol) in 81% yields as off white form.

NMR and IR Analysis Result for compound 11 prepared according to EXAMPLE 4 is as follows. The structure of the compound 11 is represented by the following Chemical Formula 11.

[Chemical Formula 11]

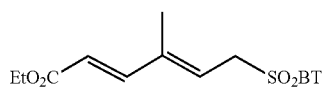

Data for Compound 11: $R_f$=0.46 (2:1 EtOAc/hexane); m.p.: 120-122° C.; $^1$H-NMR δ=1.29 (t, J=7.2 Hz, 3H), 1.76 (d, J=1.2 Hz, 3H), 4.20 (q, J=7.2 Hz, 2H), 4.44 (d, J=8.4 Hz, 2H), 5.87 (dt, $J_d$=0.8 Hz, $J_t$=8.4 Hz, 1H), 5.89 (d, J=15.6 Hz, 1H), 7.26 (d, J=15.6 Hz, 1H), 7.58-7.68 (m, 2H), 8.00-8.04 (m, 1H), 8.21-8.25 (m, 1H) ppm; $^{13}$C-NMR δ=12.7, 14.2, 54.8, 60.6, 120.1, 122.0, 122.4, 125.4, 127.8, 128.2, 136.9, 142.0, 146.5, 152.6, 165.3, 166.6 ppm; IR (neat) v=2982, 1710, 1623, 1466, 1414, 1394, 1300, 1234, 1146, 1023, 903, 854, 756 cm$^{-1}$; HRMS (ESI) calcd for $C_{16}H_{12}NO_4S_2Na$ 374.0491, found 374.0494.

Example 5: Preparation of Ethyl (2E,4E,6E,8E,10E,12E)-4,8,13-trimethyl-14-oxotetradeca-2,4,6,8,10,12-hexaenoate (16)

To a stirred solution of sulfone 11 (2.55 g, 7.26 mmol, 2.0 equiv.) and $C_{10}$ dialdehyde 12 (0.60 g, 3.65 mmol) in $CH_2Cl_2$ (50 mL) was slowly added DBU (1.38 g, 9.10 mmol) under argon atmosphere. The mixture was stirred at room temperature for 12 hours and quenched with 10% $NH_4Cl$ solution. The mixture was extracted with $CH_2Cl_2$, dried over anhydrous $Na_2SO_4$, filtered, and concentrated under reduced pressure. The crude product was purified by $SiO_2$ flash column chromatography (5%-15% EtOAc in hexanes) to give mono-coupled product 16 (0.77 g, 2.56 mmol) in 70% yield as deep red powder.

NMR and IR Analysis Result for compound 16 prepared according to EXAMPLE 5 is as follows. The structure of the compound 16 is represented by the following Chemical Formula 16.

[Chemical Formula 16]

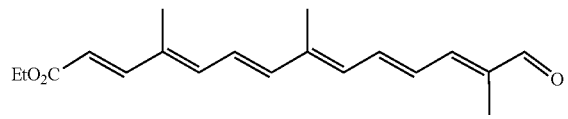

Data for Compound 16: $R_f$=0.38 (1:4 EtOAc/hexane); m.p.: 148-150° C.; $^1$H-NMR δ=1.31 (t, J=7.2 Hz, 3H), 1.90 (s, 3H), 1.97 (s, 3H), 2.05 (s, 3H), 4.23 (q, J=7.2 Hz, 2H), 5.93 (d, J=16.0 Hz, 1H), 6.39 (d, J=11.6 Hz, 1H), 6.51 (d, J=11.6 Hz, 1H), 6.52 (d, J=14.8 Hz, 1H), 6.75 (dd, J=14.8, 11.6 Hz, 2H), 6.97 (d, J=11.6 Hz, 1H), 7.03 (dd, J=14.8, 11.6 Hz, 1H), 7.38 (d, J=16.0 Hz, 1H), 9.47 (s, 1H) ppm; $^{13}$C-NMR δ=9.6, 12.7, 13.0, 14.3, 60.3, 117.3, 126.3, 128.7, 133.1, 134.9, 137.1, 137.6, 138.6, 140.7, 140.8, 148.4, 148.5, 167.3, 194.5 ppm; IR (neat) v=2977, 2915, 2803, 2708, 1740, 1660, 1587, 1442, 1376, 1303, 1170, 975, 835 cm$^{-1}$; HRMS (ESI) calcd for $C_{19}H_{24}O_3Na$ 323.1618, found 323.1621.

Example 6-1: Preparation of Diethyl (2E,4E,6E,8E,10E,12E,14E,16E,18E)-4,8,13,17-tetramethylicosa-2,4,6,8,10,12,14,16,18-nonaenedioate 2 from Compound 16

To a stirred solution of BT-sulfone 11 (1.07 g, 3.04 mmol, 2 equiv.) and mono-coupled product 16 (0.46 g, 1.53 mmol) in $CH_2Cl_2$ (40 mL) was slowly added DBU (0.60 g, 3.97 mmol) under argon atmosphere. The mixture was stirred at room temperature for 24 hours and quenched with 10% $NH_4Cl$ solution. The mixture was extracted with $CH_2Cl_2$, dried over anhydrous $Na_2SO_4$, filtered, and concentrated under reduced pressure. The crude product was purified by $SiO_2$ flash column chromatography (5% EtOAc in hexanes) to give bixin ethyl ester 2 (0.47 g, 1.07 mmol) in 70% yield as deep red powder.

Example 6-2: Preparation of Diethyl (2E,4E,6E,8E,10E,12E,14E,16E,18E)-4,8,13,17-tetramethylicosa-2,4,6,8,10,12,14,16,18-nonaenedioate 2 from Compound 11 and Compound 12

To a stirred solution of BT-sulfone 11 (2.14 g, 6.09 mmol, 4.0 equiv.) and $C_{10}$ dialdehyde 12 (0.25 g, 1.52 mmol) in $CH_2Cl_2$ (50 mL) was slowly added DBU (1.01 g, 6.68 mmol) under argon atmosphere. The mixture was stirred at room temperature for 12 hours and quenched with 10% $NH_4Cl$ solution. The mixture was extracted with $CH_2Cl_2$, dried over anhydrous $Na_2SO_4$, filtered, and concentrated under reduced pressure. The crude product was purified by $SiO_2$ flash column chromatography (5%-15% EtOAc in hexanes) to give mono-coupled product 16 (0.24 g, 0.80 mmol) and bixin ethyl ester 2 (80 mg, 0.18 mmol) in 53% and 12% yields, respectively as deep red powder.

NMR and IR Analysis Result for compound 2 prepared according to EXAMPLE 6-1 and EXAMPLE 6-2 is as follows. The structure of the compound 2 is represented by the following Chemical Formula 2.

[Chemical Formula 2]

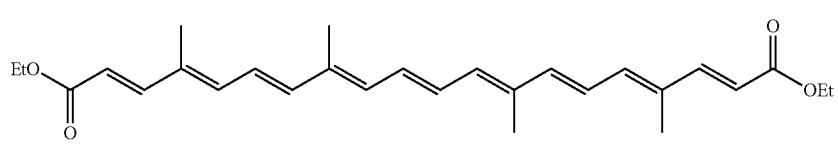

Data for Compound 2: $R_f$=0.41 (1:4 EtOAc/hexane); m.p.: 170-172° C.; $^1$H-NMR δ=1.31 (t, J=7.2 Hz, 6H), 1.95 (s, 6H), 1.99 (s, 6H), 4.22 (q, J=7.2 Hz, 4H), 5.88 (d, J=15.6 Hz, 2H), 6.25-6.40 (m, 2H), 6.50 (d, J=12.0 Hz, 2H), 6.51 (d, J=14.4 Hz, 2H), 6.63 (dd, J=14.4, 12.0 Hz, 2H), 6.64-6.74 (m, 2H), 7.38 (d, J=15.6 Hz, 2H) ppm; $^{13}$C-NMR δ 12.7, 12.8, 14.4, 60.2, 116.4, 124.5, 131.1, 133.6, 134.7, 136.9, 139.3, 141.6, 148.8, 167.5 ppm; IR (neat) ν=2920, 2852, 1703, 1614, 1563, 1457, 1366, 1304, 1259, 1165, 1027, 976, 841, 753 cm$^{-1}$; HRMS (ESI) calcd for $C_{28}H_{36}O_4Na$ 459.2506, found 459.2509.

Experimental Example 1: Confirmation of Yield of Bromohydrin Compound

The yield of the bromohydrin compound represented by Chemical Formula 7, which was manufactured according to Examples 1-1 and 1-2, was confirmed, and the results are shown in Table 1 below.

TABLE 1

| No | Metal base | Additive | Reaction condition | Yield | | |
|---|---|---|---|---|---|---|
| | | | | Chemical Formula 7 | Chemical Formula 8 | Chemical Formula 9 |
| 1 | LDA | — | −78°C., 4 h | 46 | 13 | 7 |
| 2 | LiHMDS | — | −78°C., 4 h | 43 | 15 | 8 |
| 3 | KHMDS | — | −78°C., 4 h | — | — | — |
| 4 | LDA | $BF_3 \cdot OEt_2$ | −78°C., 4 h | — | — | — |
| 5 | LDA | $Mg(N-i-Pr_2)_2$ | −78°C., 2 h then rt, 4 h | 76 | — | — |
| 6 | LDA | $MgBr_2$ | −78°C., 2 h then rt, 4 h | 77 | — | — |

As a result, as shown in Table 1 above, the enolate generated from the compound of Chemical Formula 5 by LDA was reacted with the compound of Chemical Formula 6 at −78° C., thus obtaining mono- and di-epoxide products 8 and 9 at yields of 13% and 7% and the bromohydrin compound represented by Chemical Formula 7 to be manufactured by the present invention at a yield of 43%. Further, even when LiHMDS was used as a metal-amide base, the result that was obtained was similar to that of the reaction using LDA, but no compound was generated when KHMDS was used as the metal-amide base.

Next, in the reaction using $BF_3.OEt_2$ as an additive while using LDA as the metal-amide base, none of the bromohydrin compound represented by Chemical Formula 7 or the mono- and di-epoxide products 8 and 9 were generated. On the contrary, in the reaction using $Mg(N-i-Pr_2)_2$ or $MgBr_2$ as an additive, the epoxide product was not generated, but only the bromohydrin compound represented by Chemical Formula 7 was generated.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A sulfone compound represented by Chemical Formula 11 below:

[Chemical Formula 11]

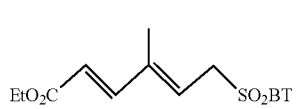

wherein the BT is

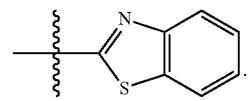 [SMILES: *c1nc2ccccc2s1]

2. A method of manufacturing a sulfone compound represented by Chemical Formula 11 below, the method comprising:
mixing and reacting an ester compound represented by Chemical Formula 15 below and a solution containing acetonitrile:

[Chemical Formula 11]

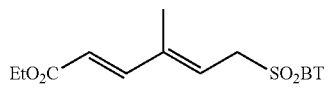

[Chemical Formula 15]

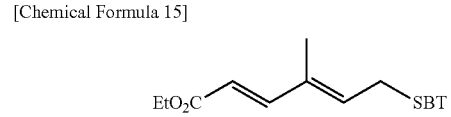

wherein the BT is

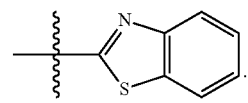 [SMILES: *c1nc2ccccc2s1]

3. The method of claim 2, wherein the solution containing the acetonitrile is manufactured by mixing a mixture of urea-$H_2O_2$ and phthalic anhydride with the acetonitrile.

4. The method of claim 2, wherein the ester compound represented by Chemical Formula 15 is manufactured by adding a compound represented by Chemical Formula 13 below to a mixture containing tetrahydrofuran, (2-ethoxy-2-oxoethyl)triphenylphosphonium bromide, and sodium hydride and performing a reaction:

[Chemical Formula 13]

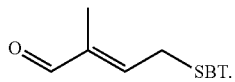

5. A method of manufacturing bixin ethyl ester represented by Chemical Formula 2 below, the method comprising:
mixing a sulfone compound represented by Chemical Formula 11 below with a compound represented by Chemical Formula 12 below or a compound represented by Chemical Formula 16 below:

[Chemical Formula 11]

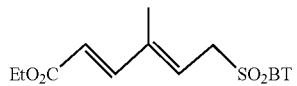

[Chemical Formula 12]

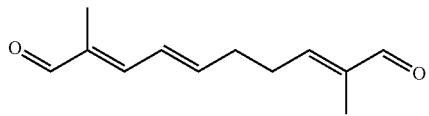

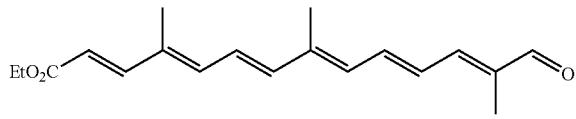

[Chemical Formula 16]

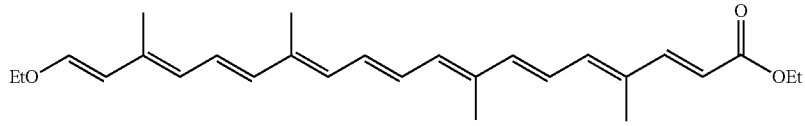

[Chemical Formula 2]

wherein the BT is

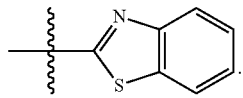 [SMILES: *c1nc2ccccc2s1]

6. The method of claim 5, further comprising:
adding DBU (1,8-diazabicycloundec-7-ene) to a mixture of the sulfone compound represented by Chemical Formula 11 and the compound represented by Chemical Formula 12 or the compound represented by Chemical Formula 16, and performing a reaction.

7. The method of claim 5, wherein the compound represented by Chemical Formula 16 is manufactured by adding DBU (1,8-diazabicycloundec-7-ene) to the sulfone compound represented by Chemical Formula 11 and an aldehyde compound represented by Chemical Formula 12 and performing a reaction.

* * * * *